(12) United States Patent
Do et al.

(10) Patent No.: US 11,806,091 B2
(45) Date of Patent: Nov. 7, 2023

(54) METHOD FOR VERIFYING MATCHING OF SURGERY TARGET, APPARATUS THEREFOR, AND SYSTEM INCLUDING SAME

(71) Applicant: CUREXO, INC., Seoul (KR)

(72) Inventors: Dae Guk Do, Seoul (KR); Geun Young Kim, Seoul (KR); Heung Soon Lim, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/798,252

(22) PCT Filed: Jan. 27, 2021

(86) PCT No.: PCT/KR2021/001087
§ 371 (c)(1),
(2) Date: Aug. 8, 2022

(87) PCT Pub. No.: WO2021/162287
PCT Pub. Date: Aug. 19, 2021

(65) Prior Publication Data
US 2023/0076292 A1    Mar. 9, 2023

(30) Foreign Application Priority Data
Feb. 12, 2020    (KR) .................. 10-2020-0017019

(51) Int. Cl.
*A61B 34/20*    (2016.01)
*A61B 34/00*    (2016.01)
(Continued)

(52) U.S. Cl.
CPC .............. *A61B 34/20* (2016.02); *A61B 34/25* (2016.02); *A61B 34/30* (2016.02);
(Continued)

(58) Field of Classification Search
CPC combination set(s) only.
See application file for complete search history.

(56) References Cited

U.S. PATENT DOCUMENTS

| 2005/0215879 A1 | 9/2005 | Chuanggui |
| 2006/0079759 A1 | 4/2006 | Vaillant et al. |

(Continued)

FOREIGN PATENT DOCUMENTS

| JP | 2018-534960 A | 11/2018 |
| KR | 10-2015-0102936 A | 9/2015 |

(Continued)

*Primary Examiner* — Scott Luan
(74) *Attorney, Agent, or Firm* — Bridgeway IP Law Group, PLLC; Jihun Kim

(57) ABSTRACT

Proposed are a method of verifying matching of a surgical target, an apparatus therefor, and a system including the same, the method including: preparing a three-dimensional (3D) model including shape information about the surgical target; acquiring information about positions and postures of the surgical target and a target marker attached to the surgical target through a tracker; performing matching with the 3D model by deriving a correlation in position and posture between the surgical target and the target marker; tracking change in the position and posture of a probe tip moving along a surface of the surgical target; and generating and displaying matching verification information including a 3D graphic icon, which represents a relative positional relationship between the probe tip and the 3D model, corresponding to change in at least one of the position and posture of the probe tip.

11 Claims, 7 Drawing Sheets

(51) Int. Cl.
*A61B 34/30* (2016.01)
*A61B 34/10* (2016.01)
*A61B 90/00* (2016.01)

(52) U.S. Cl.
CPC ... *A61B 2034/105* (2016.02); *A61B 2034/107* (2016.02); *A61B 2034/2065* (2016.02); *A61B 2034/2072* (2016.02); *A61B 2090/367* (2016.02); *A61B 2090/3916* (2016.02)

(56) References Cited

U.S. PATENT DOCUMENTS

| | | |
|---|---|---|
| 2014/0188121 A1 | 7/2014 | Lavallee |
| 2014/0206990 A1 | 7/2014 | Epstein et al. |
| 2015/0342462 A1 | 12/2015 | Park et al. |
| 2019/0201155 A1 | 7/2019 | Gupta et al. |
| 2020/0237441 A1 | 7/2020 | Zuhars et al. |

FOREIGN PATENT DOCUMENTS

| | | |
|---|---|---|
| KR | 20150138902 A | 12/2015 |
| KR | 1655309 B1 | 9/2016 |
| KR | 20180071328 A | 6/2018 |

METHOD FOR VERIFYING MATCHING OF SURGERY TARGET, APPARATUS THEREFOR, AND SYSTEM INCLUDING SAME

TECHNICAL FIELD

The disclosure relates to a method of verifying matching of a surgical target, an apparatus therefor, and a system including the same, and more particularly to a method of verifying matching of a surgical target to check a degree of spatial matching between the surgical target and a surgical image, an apparatus therefor, and a system including the same.

BACKGROUND ART

With recent development of medical technology, navigation surgery using a robot and a computer system has been actively introduced, and such surgery is also being applied to the field of artificial joint surgery.

In the case of a knee joint, when external injury, various types of infection, and diseases cause pains and physical impairments in the knee joint, the whole or part of the knee joint is treated through orthopedic surgery based on replacement. About 10 to 30% of patients who will undergo partial replacement have a knee joint of which the inside has worn.

Among robots used in such orthopedic surgery for the joints, there is a robot that performs the whole surgical procedure automatically. Such a surgical robot automatically cuts bones along a previously planned path without human intervention.

For the knee joint surgery using the surgical robot, it is necessary to perform a spatial matching process between a surgical target and its shape model in advance by first mounting an optical marker to the surgical target, and then tracking the position and posture of the optical marker with an optical sensor. Further, it is required to check whether a result of matching is suitable.

A conventional method of verifying the matching of a surgical target generally employs a method of checking a quantitative value for the result of matching, or a method of checking matching degrees of a plurality of previously registered points.

However, the former method makes it difficult for a user to determine whether the result of matching is suitable because the matching is simply expressed as the quantitative value, and the latter method has a problem that only the matching degrees of the previously registered points are checked and it is therefore impossible to check matching degrees in other areas.

(Patent Document 1 of Related Art) Korean Patent Publication No. 102015-0102936 (Sep. 9, 2015).

DISCLOSURE

Technical Problem

To solve the foregoing problems, an aspect of the disclosure is to provide a method of verifying matching intuitively and visually. Further, an aspect of the disclosure is to provide a method of verifying matching of a surgical target, an apparatus therefor, and a system including the same, in which it is possible to intuitively check a matching degree of not a single point but a certain continuous area. Further, an aspect of the disclosure is to provide a method of verifying matching of a surgical target, an apparatus therefor, and a system including the same, in which matching is performed again for an area that needs re-matching when a result of matching is unsuitable.

Technical Solution

The aspects of the disclosure may be achieved by providing a method of verifying matching of a surgical target, the method including: preparing a three-dimensional (3D) model including shape information about the surgical target; acquiring information about positions and postures of the surgical target and a target marker attached to the surgical target through a tracker; performing matching with the 3D model by deriving a correlation in position and posture between the surgical target and the target marker; tracking change in the position and posture of a probe tip moving along a surface of the surgical target; and generating matching verification information including a 3D graphic icon, which represents a relative positional relationship between the probe tip and the 3D model, corresponding to change in at least one of the position and posture of the probe tip, and displaying the matching verification information as an image.

Meanwhile, the aspect of the disclosure may also be achieved by providing a method of verifying matching of a surgical target, the method including: receiving the information about the positions and postures of the surgical target and the target marker attached to the surgical target, acquired through the tracker; performing the matching between the surgical target and the 3D model by deriving the correlation in position and posture between the surgical target and the target marker; receiving information about the position and posture of the probe tip moving along the surface of the surgical target, acquired through the tracker; and generating the matching verification information including the 3D graphic icon, which represents a relative positional relationship between the probe tip and the 3D model, corresponding to change in the position and posture of the probe tip, and displaying the matching verification information as an image.

Further, the generating the matching verification information and displaying the image may include generating the 3D graphic icon, which represents a plurality of spheres different in radius from each other and using the position of the probe tip as a center, and displaying the 3D graphic icon on the 3D model.

Further, the generating the matching verification information and displaying the image may include changing a shape of the 3D graphic icon to represent the relative positional relationship between the position of the probe tip and the surface of the 3D model.

In addition, the generating the matching verification information and displaying the image may include displaying the image varied in viewpoint depending on change in the position or posture of the probe tip.

Further, the image showing the matching verification information may include a first area in which a first image varied in viewpoint for the 3D model depending on change in the position or posture of the probe tip is displayed, and a first area in which a first image is displayed with at least one fixed viewpoint for the 3D model.

The plurality of spheres may be represented to be visually distinguished from each other.

Further, the method may further include quantitatively calculating and displaying a result of the matching, wherein the quantitatively calculating and displaying the result of the matching may include at least one of: calculating and displaying a deviation of a distance between a plurality of points on the surgical target acquired for the matching and a plurality of points on the corresponding 3D model; calculating and displaying a distance between a point at which the probe tip is located corresponding to movement of the probe and a landmark point on the 3D model; and calculating and displaying a distance between a point at which probe tip is located corresponding to movement of the probe and a corresponding point on the 3D model.

Meanwhile, the aspects of the disclosure may be achieved by providing an apparatus for verifying matching of a surgical target, the apparatus including: a signal receiver configured to receive information about positions and postures of the surgical target and a target marker attached to the surgical target, acquired through a tracker; a target matcher configured to perform the matching between the surgical target and a three-dimensional (3D) model by deriving a correlation in position and posture between the surgical target and the target marker; and a matching verifier configured to generate matching verification information including a 3D graphic icon, which represents a relative positional relationship between the probe tip and the image model, based on change in the information about the position and posture of the probe tip moving along a surface of the surgical target, received through the data input unit.

In addition, the matching verifier may generate the 3D graphic icon, which represents a plurality of spheres different in radius from each other and using the position of the probe tip as a center, and displays the 3D graphic icon on the 3D model, and the plurality of spheres may be represented to be visually distinguished from each other.

Further, the matching verifier may generate the matching verification information so that a first image having at least one fixed viewpoint for the 3D model and a second image varied in viewpoint depending on change in the position and posture of the probe tip can be respectively displayed in separate areas.

Meanwhile, the aspects of the disclosure may be achieved by providing a system for verifying matching of a surgical target, the system including: a tracker configured to track positions and postures of a target marker attached to the surgical target and a probe; a memory configured to store a three-dimensional (3D) model having shape information about the surgical target acquired before surgery; a target matcher configured to perform matching with the 3D model by deriving a correlation in position and posture between the surgical target and the target marker attached to the surgical target; a matching verifier configured to generate matching verification information including a 3D graphic icon, which represents a relative positional relationship between the probe tip and the image model, based on change in the information about the position and posture of the probe tip moving along a surface of the surgical target, acquired by the tracker; and a display unit configured to display an image based on the matching verification information.

Here, the matching verifier may generate the 3D graphic icon, which represents a plurality of spheres different in radius from each other and using the position of the probe tip as a center, and displays the 3D graphic icon on the 3D model, and the plurality of spheres may be represented to be visually distinguished from each other.

Advantageous Effects

As described above, there are provided a method of verifying matching of a surgical target according to the disclosure, an apparatus therefor, and a system including the same, in which the matching is verified intuitively and visually. Further, it is possible to intuitively check a matching degree of not a single point but a certain continuous area. Further, when a result of matching is not suitable, the matching is performed again for only an area that needs re-matching, thereby shortening time required in the matching.

MODE FOR INVENTION

Below, embodiments of the disclosure will be described with reference to the accompanying drawings.

Figure 1:
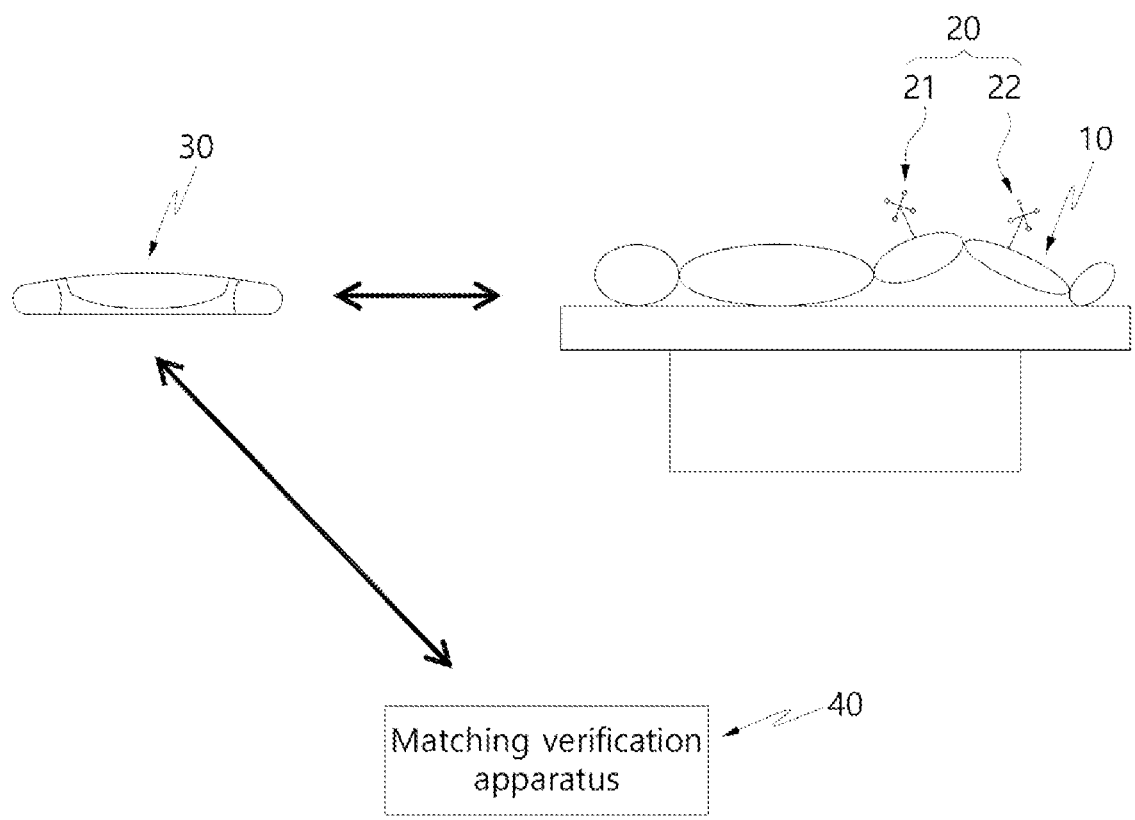
FIG. 1 schematically shows a system for verifying matching of a surgical target according to an embodiment of the disclosure.

FIG. 1 schematically shows a system for verifying matching of a surgical target according to an embodiment of the disclosure. Referring to FIG. 1, the system for verifying image matching of a surgical target according to an embodiment of the disclosure includes target markers 20 attached to a surgical target 10, a tracker 30, and a matching verification apparatus 40.

The surgical target 10 refers to a target for surgery. According to an embodiment of the disclosure, a knee joint between the femur and the tibia will be described as an example of the surgical target 10, and thus the target markers 20 are attached to the femur and the tibia, respectively. Further, according to the disclosure, the term 'surgical target' in the disclosure may be used in a broad sense including surgical objects such as the femur and the tibia, and may also be used in a narrow sense indicating a specific position or surgical site of the surgical target such as an implant origin or a joint center. During the matching of the surgical target 10, the positions corresponding to a plurality of points of the surgical target 10 are registered by a user using a probe 50.

An optical marker may be used for the target marker 20 and the probe 50, and include three or four bars branching in different directions with respect to a central point and respectively formed with highly reflective ball markers at the ends thereof.

The tracker 30 is configured to track the positions and postures of the probe 50 and the target markers 20 attached to the surgical target 10. The tracker 30 detects the positions and postures of markers on three-dimensional (3D) spatial coordinates, and transmits the detected positions and postures to the matching verification apparatus 40 (to be described later). According to an embodiment of the disclosure, an optical tracking system (OTS) may be used as an example of the tracker 30.

The matching verification apparatus 40 for the surgical target 10 is configured to verify the spatial matching and matching result of the surgical target 10, and may include a computer (or a processor) and a display unit. The matching verification apparatus 40 for the surgical target 10 may be provided as an independent apparatus. As necessary, the computer (or the processor) and the display unit may be separately provided in such a way that the computer (or the processor) is provided in a surgical robot and the display unit is connected to and integrated into the tracker 30. In this case, the computer (or the processor) provided in the surgical robot is connected to the tracker 30, receives the position/posture information of the markers, processes the matching and the matching result, and transmits the matching results to the display unit.

Figure 2:
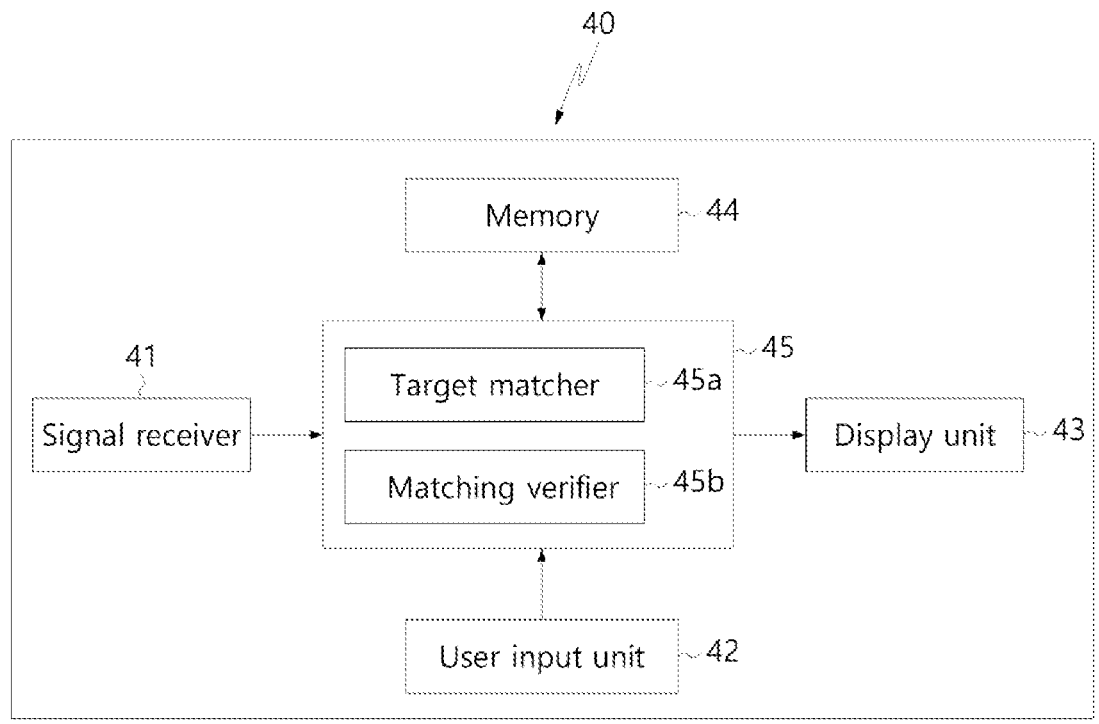
FIG. 2 is a control block diagram of an apparatus for verifying matching of a surgical target according to an embodiment of the disclosure.

FIG. 2 is a control block diagram of the matching verification apparatus 40 for the surgical target according to an embodiment of the disclosure. Referring to FIG. 2, the matching verification apparatus 40 for the surgical target according to an embodiment of the disclosure includes a signal receiver 41, a user input unit 42, a display unit 43, a memory 44, and a controller 45.

The signal receiver 41 is configured to receive a signal from the outside, and may for example include a high-definition multimedia interface (HDMI) connector and a D-sub connector for connection with the external devices, or a communication module for connection with a wired/wireless network such as the Internet. The signal receiver 41 may include a wired/wireless communication module for interworking with the tracker 30.

The user input unit 42 is configured to receive a command from a user and transmit the command to the controller 45 (to be described later), and may include various input units such as a keyboard, a mouse or a button.

The display unit 43 is configured to display an image on a screen, and may be implemented as a liquid crystal display (LCD) panel, a light emitting diode (LED) panel, an organic light emitting diode (OLED) panel, etc.

Here, the user input unit 42 and the display unit 43 may be physically separated from the other elements. For example, the signal receiver 41, the controller 45, and the memory 44 may be integrated into the main body of the surgical robot, and the user input unit 42 and the display unit 43 may be configured as a separate apparatus connected to the tracker 30 and the surgical robot by communication.

The memory 44 may be configured to store various operating systems (OS), middleware, platform, and various applications of the matching verification apparatus 40 for the surgical target, and may be configured to store a program code and video and audio signals and data subjected to signal processing. The memory 44 is configured to store a 3D model 10a having shape information about the surgical target 10, which has been acquired before surgery. Here, the 3D model 10a of the surgical target 10 may for example be generated from a set of image data such as a patient's computed tomography (CT) or magnetic resonance imaging (MRI) images.

The controller 45 is configured to perform overall control of the matching verification apparatus 40 for the surgical target based on a user input received through the user input unit 42 or an internal program. The controller 45 may include a program code for signal processing and control, and a processor for executing a program. The controller 45 performs position tracking and matching based on the position/posture information about the target markers 20 and the probe 50 received from the tracker 30 through the signal receiver 41, and generates the matching verification information about the matching result which represents a matching degree.

Referring to FIG. 2, the controller 45 includes a target matcher 45a and a matching verifier 45b.

The target matcher 45a performs matching between the surgical target 10 and the 3D model 10a having the shape information about the surgical target 10 based on the position/posture information of the target marker 20 and the probe 50 acquired from the tracker 30. The target matcher 45a derives a position/posture correction between the surgical target 10 and the target markers (or bone markers) 20 attached to the surgical target from the position/posture information of the target marker 20 and the probe 50.

For example, after the target markers 20 are mounted to the surgical target 10, a plurality of specific points of a preset surgical target 10 and the positions/postures of the target markers 20 are detected by the probe 50 at the same time. The target matcher 45a receives information about the positions/postures of the target markers 20 and the specific points indicated by the probe 50 acquired through the tracker 30, and derives a position/posture correlation between the target marker 20 and the surgical target 10 from the received information, thereby performing matching with the 3D model 10a of the surgical target 10 previously stored in the memory 44. The target matcher 45a may be embodied including a program code and/or software to calculate the position and perform the matching.

The matching verifier 45b is configured to generate matching verification information about a matching result of the target matcher 45a, and generates the matching verification information including a 3D graphic icon representing a relative positional relationship between the tip of the probe 50 and the image model, based on change in position and posture information about the tip of the probe 50 moving along the surface of the surgical target 10. Further, the matching verifier 45b may quantitatively calculate the matching result. Meanwhile, quantitative values of the matching degree and the matching verification information generated through the matching verifier 45b are provided to the display unit 43 and displayed as an image. With this, a user can intuitively and visually recognize the matching degree. The matching verifier 45b may be embodied including a program code and/or software to calculate the matching result and generate the matching verification information and graphics.

Figure 3:
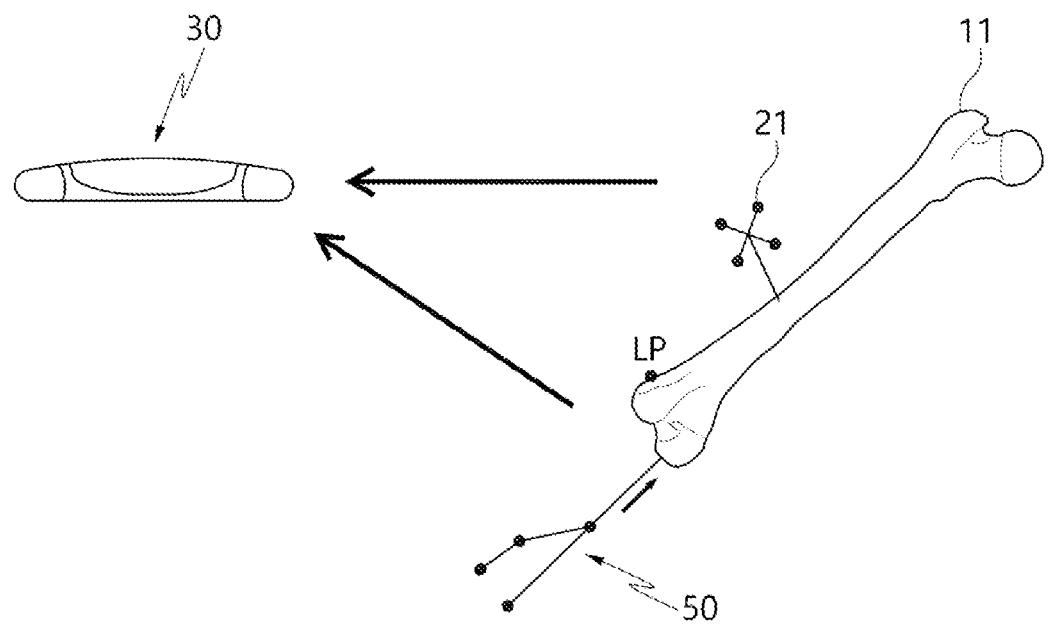
FIG. 3 is a diagram for illustrating operations of a controller according to an embodiment of the disclosure.

FIG. 3 is a diagram for illustrating operations of the controller 45 according to an embodiment of the disclosure. Referring to FIG. 3, for example, the femur 11 is illustrated as the surgical target 10, and the target marker 21 is attached to the femur.

Referring to FIG. 3, a user uses the probe 50 to register positions corresponding to designated points of the preset surgical target 11. The tracker 30 tracks the positions/postures of the target marker 21 and the probe 50 indicating the designated points on the surface of the surgical target 11, and transmits the tracked positions/postures to the matching verification apparatus 40. The matching verification apparatus 40 performs matching with the previously stored 3D model 10a corresponding to the surgical target 11, based on the position/posture information of the probe 50 and the target marker 21 received from the tracker 30. In general, four views such as distal, posterior, medial, and anterior views of the 3D model 10a corresponding to the surgical target 10 or 11 are switched over in sequence, and points corresponding to the positions of points previously set in the switched view are indicated by the probe 50, thereby registering the corresponding positions by receiving the position/posture information of the probe 50 and the target marker 21. Here, about 20 to 40 points are registered. In FIG. 3, 'LP' is the abbreviation for a landmark point, and refers the reference points for the postures of the surgical target 10 or 11. Thus, the matching is performed while a user sequentially designates the corresponding points with the probe 50 one by one and the matching verification apparatus 40 registers the designated points.

The position/posture correlation between the probe 50 and the 3D model 10a corresponding to the surgical target 10 or 11 in a spatial relationship after the matching of FIG. 3 is expressed as follows.

$$^{P}T_{B} = (^{OTS}T_{P})^{-1} \times {}^{OTS}T_{BM} \times {}^{BM}T_{B}$$ [Equation 1]

(where, PTB is a position/posture correlation between the probe 50 and the surgical target 10 or 11, OTSTP is a transformation matrix of the probe 50 relative to the tracker 30, OTSTBM is a transformation matrix of the target marker 21 relative to the tracker 30, and BMTB is a transformation matrix of the surgical target 10 or 11 relative to the target marker 21)

When the registration of the plurality of preset points is completed, the matching verifier 45b generates the matching verification information about the matching result. The matching verifier 45b generates a 3D graphic icon A, in which the position of the tip of the probe 50 is represented, to be displayed on the 3D model 10a, so that a relative positional relationship with the 3D model 10a can be represented based on change in the position and posture information of the tip of the probe 50.

Figure 4:
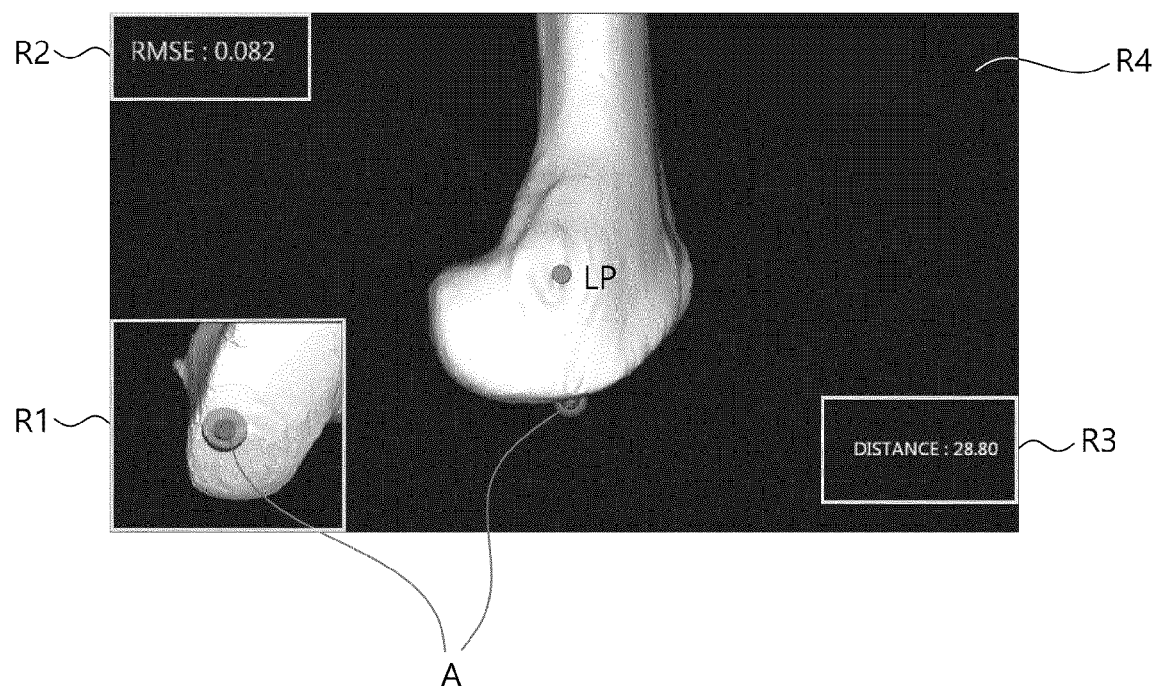
FIG. 4 shows an example of matching verification information generated by a matching verifier and displayed as an image according to an embodiment of the disclosure.

FIG. 4 shows an example of the matching verification information generated by the matching verifier 45b and displayed as an image according to an embodiment of the disclosure. Referring to FIG. 4, the image showing the matching verification information according to the disclosure has a first area where a first image varied in a view point of the image depending on change in the position or posture of the tip of the probe 50 is displayed. In the image showing the matching verification information, the first image displayed on the area R1 represents the 3D model 10a in the viewpoint viewed by the tip of the probe 50 based on the position/posture information of the probe 50. The matching verifier 45b uses the tip of the probe 50 as the center and an extension line connected to the tip and oriented in a specific direction as the axis of posture, and gives a shape to the position of the tip of the probe 50 on a partial area of the 3D model 10a viewed from the viewpoint of the corresponding axis, thereby generating the matching verification information. Therefore, the viewpoint and the area for displaying the image of the matching verification information are varied depending on the change in the position or posture of the tip of the probe 50. In other words, when the position and posture of the tip of the probe 50 are changed while the tip of the probe 50 moves sliding on the surface of the surgical target 10 or 11, the first image of the matching verification information displayed in the area R1 is displayed relatively changing the position and posture of the 3D model 10a according to the change in the position/posture of the tip of the probe 50, so that a user can intuitively check the relatively relationship with the 3D model 10a in real time while scratching the surface of the surgical target 10 or 11 with the tip of the probe 50.

Referring back to FIG. 4, 'A' indicates the 3D graphic icon A representing the position of the tip of the probe 50, so that a user can know where the tip of the probe 50 is currently located on the 3D model 10a corresponding to the surgical target 10 or 11 through the 3D graphic icon A. Here, the 3D graphic icon A giving a shape to the position of the tip of the probe 50 does not simply represent the position of the tip of the probe 50 but itself represents a relative positional relationship with the 3D model 10a.

To this end, the 3D graphic icon A giving a shape to the position of the tip of the probe 50 may represent a relative positional relationship with the 3D model 10a by a plurality of spheres using the position of the tip of the probe 50 as the center and having different radii.

Figure 5:
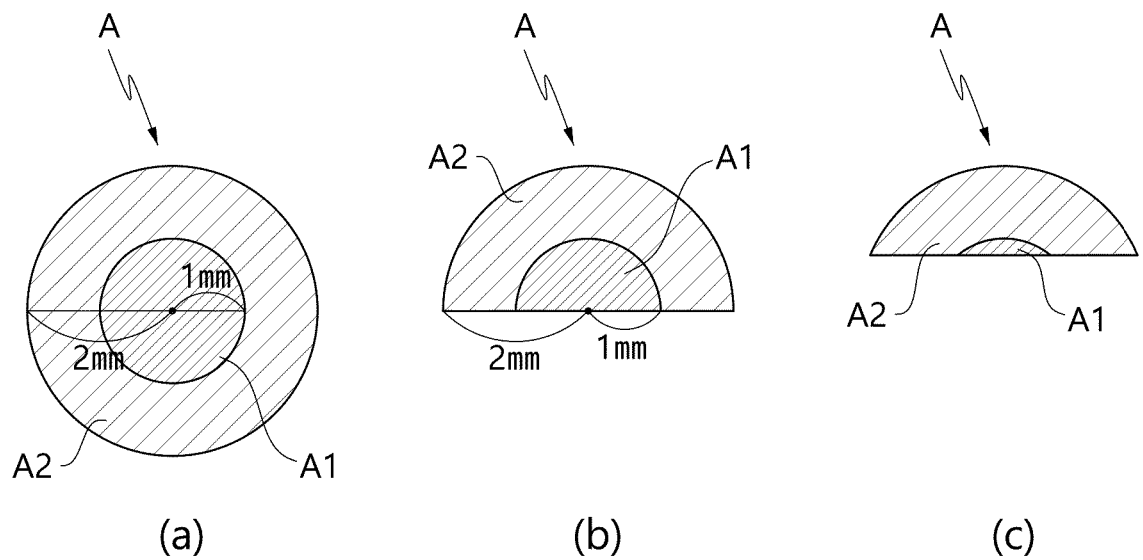
FIG. 5 shows an example of a 3D graphic icon in which a position of a probe tip is represented according to an embodiment of the disclosure.

FIG. 5 shows an example of the 3D graphic icon A in which the position of the tip of the probe 50 is represented according to an embodiment of the disclosure. Referring to FIG. 5, the 3D graphic icon A representing the tip of the probe 50 may include two spheres A1 and A2 having the same center and different radii. In FIG. 5, A1 indicates a circle having a radius of 1 mm, and A2 indicates a circle having a radius of 2 mm. The center of the 3D graphic icon A, A1 or A2 corresponds to the tip of the probe 50, i.e., a point where the tip of the probe 50 is located. When the tip of the probe 50 is in contact with the surface of the surgical target 10 or 11, a partial area of the sphere, the center of which indicates the position of the tip of the probe 50, is located inside the 3D model 10a, and therefore the partial area of the sphere that entered the 3D model 10a is not displayed in the first image, thereby making the sphere be varied in shape depending on the viewpoints. Thus, the 3D graphic icon A representing the position of the tip of the probe 50 may be displayed so that a circle can be entirely or partially seen according to position and posture relationships with the surgical target 10 or 11. In this way, the 3D graphic icon A according to the disclosure is varied in shape depending on a relative positional relationship between the tip of the probe 50 and the surface of the 3D model 10a, so that a user can intuitively know the relative positional relationship, for example, a distance or the like between the shape of the 3D model 10a and the point on the surgical target 10 or 11 where the tip of the probe 50 is currently, by changing the position and posture of the probe 50 while looking at the screen.

In addition, according to the disclosure, the 3D graphic icon A is represented with the overlapped spheres A1 and A2 different in radius from each other, and the spheres are displayed with different colors or different contrasts so as to be visually distinguished from each other. Thus, a user can intuitively know a relative positional relationship, for example, a distance or a space between the 3D model 10a and the tip of the probe 40, based on the shape of the 3D graphic icon A. Further, a user can intuitively recognize a relative positional relationship, e.g., a distance or a space between the 3D model 10a and the surface of the surgical target 10 or 11, i.e., the tip of the probe 40 not at a specific point of the surgical target 10 or 11 but in certain continuous areas, while scratching the surface of the surgical target 10 or 11 with the tip of the probe 50.

In FIG. 5, (a) shows a case where 100% of the two spheres A1 and A2 of the 3D graphic icon A is seen based on the relative positional relationship with the 3D model 10a at the viewpoint of the tip of the probe 50. In this case, the 3D model 10a may be located behind the tip of the probe 50, or may be laterally located by 2 mm away from the tip of the probe 50. In any case, it means that the tip of the probe 50 and the 3D model 10a are spaced apart by 2 mm or more from each other. Therefore, it can be intuitively understood that a difference in the matching is 2 mm or more.

In FIG. 5, (b) shows a case where 50% of the two spheres A1 and A2 of the 3D graphic icon A is seen based on the relative positional relationship with the 3D model 10a at the viewpoint of the tip of the probe 50. In this case, it means that 50% of the two spheres of the 3D graphic icon A is located inside the 3D model 10a. In other words, it can be intuitively understood that the tip of the probe 50 is located directly on the surface of the 3D model 10a. On the other hand, (c) in FIG. 5 shows a case where about 20% of the two spheres is seen, and it means that about 80% of the two spheres A1 and A2 of the 3D graphic icon A is located inside the 3D model 10a. In other words, it can be intuitively understood that the tip of the probe 50 is located within a distance of 1 mm from the inner surface of the 3D model 10a. FIG. 5 shows that the 3D graphic icon A includes the two spheres different in radius from each other, but the 3D graphic icon A may include three to five spheres.

Referring to FIG. 4, the image showing the matching verification information according to the disclosure includes a second area where a second image having at least one fixed viewpoint for the 3D model is displayed regardless of change in the position or posture of the tip of the probe 50. In the second image that shows a positional relationship between the 3D model 10a and the tip of the probe 50 at at least one fixed viewpoint for the 3D model 10a, the 3D graphic icon A is displayed on the 3D model 10a having a specific viewpoint. In this embodiment, the second image shows two lateral views of the 3D model 10a by way of example.

Referring to FIG. 4, the first image displayed in the first area is varied in the display area and the viewpoint of the 3D model 10a depending on the position/posture of the probe 50, but the second image displayed in the second area shows the 3D model 10a having the specific viewpoint regardless of the position/posture of the probe 50. Therefore, a user can intuitively recognize a matching degree while comparing the two images based on the shape of the 3D graphic icon A representing the position of the tip of the probe 50.

FIG. 4 shows the matching verification information of when the position/posture of the probe 50 is as shown in FIG. 3, in which the tip of the probe 50 is almost at a right angle toward the surgical target 10 or 11. Therefore, while the first image of FIG. 4 shows that 100% of the 3D graphic icon A is seen as exposed on the 3D model 10a at the viewpoint of the tip of the probe 50, the second image shows that only about 50%, i.e., a hemisphere, of the sphere corresponding to the 3D graphic icon A is seen because the tip of the probe 50 is located at a lower side in the state that the viewpoint of the 3D model 10a is fixed to the lateral side. While it is impossible to accurately know the matching degree in the first image, it is shown that the matching between the surgical target 10 or 11 and the 3D model 10a at the corresponding position is almost accurately made. However, the second image is based on the fixed viewpoint, and therefore the sphere may hardly be seen at the lateral side if the point at which the tip of the probe 50 is currently located is the lowest point of curvature in the curve of the surgical target 10 or 11. Accordingly, it is difficult to know an accurate matching degree in the second image, and it is more accurate to get a viewpoint at which the 3D graphic icon A is seen as a hemisphere by controlling the posture of the probe 50 in the first image.

Figure 6:
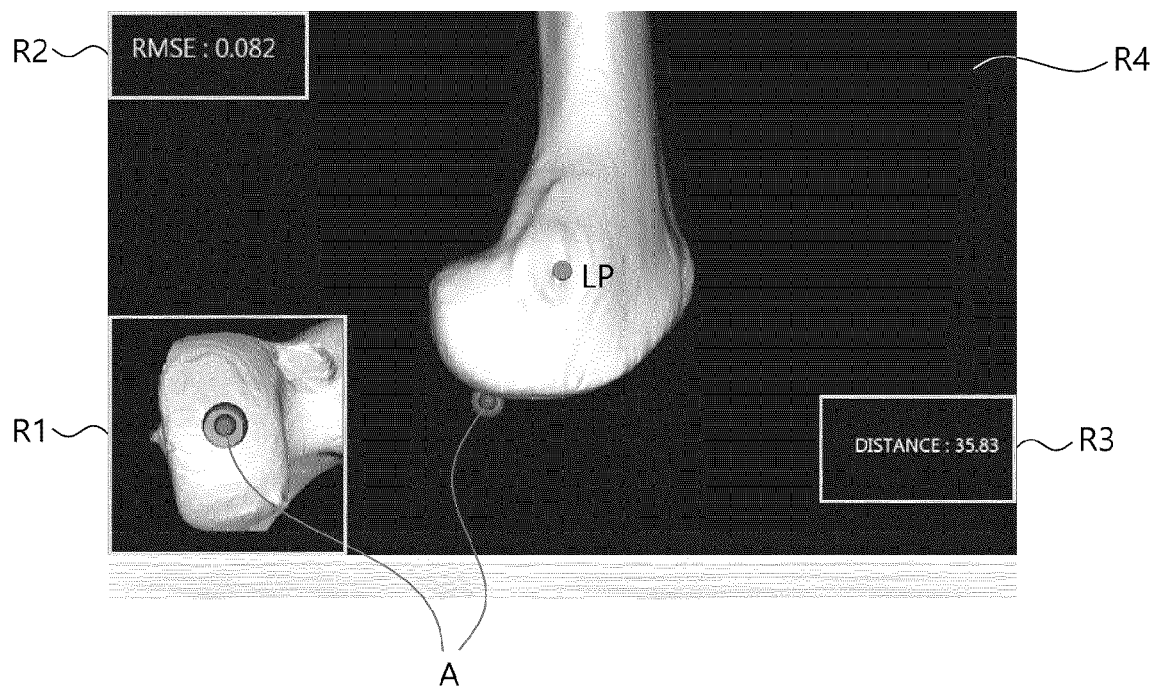
FIG. 6 shows matching verification information in a state that the posture of a probe tip is slightly turned rightward while the position of the probe tip is moved above from the position of FIG. 3 according to an embodiment of the disclosure.

FIG. 6 shows matching verification information in a state that the posture of the tip of the probe 50 is slightly turned rightward while the position of the probe tip is moved above from the position of FIG. 3 according to an embodiment of the disclosure. Like that of FIG. 4, the first image of FIG. 5 shows that 100% of the sphere, i.e., the 3D graphic icon A is seen as exposed on the 3D model 10a at the viewpoint of the tip of the probe 50. This is because the tip of the probe 50 still has the posture of facing toward the surgical target 10 or 11. However, in the second image, the sphere is not entirely but partially represented, i.e., almost 80% or more of the sphere is exposed because the viewpoint of the 3D model 10a is fixed to the lateral side and the tip of the probe 50 is located at the lower side. Therefore, it can be intuitively understood that a deviation of at least 1.5 mm is present between the surgical target 10 or 11 and the 3D model 10a even if the tip of the probe 50 is currently located at the highest point of curvature in the curve of the surgical target 10 or 11.

As above, the matching verification information according to the disclosure shows the position of the tip of the probe 50 represented with the plurality of spheres having different radii, so that a user can intuitively know how far the point of the surgical target 10 or 11 indicated by the tip of the probe 50 is approximately located from the 3D model 10a, based on the shape of the 3D graphic icon A represented on the 3D model 10a while changing the posture of the tip of the probe 50. Further, the corresponding viewpoint and position of the 3D model 10a are displayed according to the change in the position/posture of the probe 50, thereby making it possible to easily check the matching degree in an area desired to be checked while scratching the surface of the surgical target 10 or 11 with the tip of the probe 50. Thus, it is possible to intuitively know a matching deviation degree, i.e., which part of the surgical target 10 or 11 is not suitably matched.

The matching verifier 45b may calculate a matching result as a quantitative value, and show this value as included in the matching verification information. For example, the matching verifier 45b may calculate a root mean square(d) error (RMSE) value, which is related to a deviation of a distance between a plurality of points on the surgical target 10 or 10 acquired for the matching and a plurality of points on the corresponding 3D model 10a, as a suitability evaluation value for the matching result. Referring to FIG. 4, the RMSE value is displayed in a third area. With this value, a user can numerically check the matching suitability.

Figure 7:
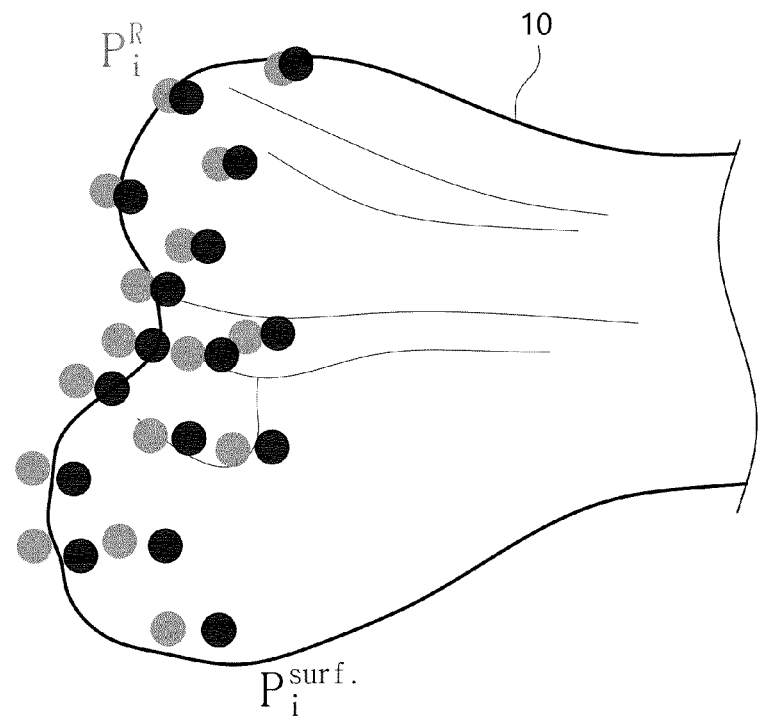
FIG. 7 is a diagram for illustrating a method by which a matching verifier calculates matching suitability according to an embodiment of the disclosure.

FIG. 7 is a diagram for illustrating a method by which the matching verifier 45b calculates the matching suitability according to an embodiment of the disclosure. In FIG. 7, the light gray points PiR denote the points acquired in the surgical target 10 or 11 for the matching, and the black points Pisurf. denote the points closest to the matching points on the 3D model 10a.

The matching verifier 45b calculates the deviation between the matching points acquired for the matching and the points closest to the matching points on the 3D model 10a by the following equation.

$$\text{RMS Error} = \sqrt{\frac{\sum_{i}^{N} \{err \cdot (P_i^R, P_i^{surf.})\}^2}{N}} \qquad \text{[Equation 2]}$$

(where, PiR is the point acquired from the surgical target 10 or 11 for the matching, Pisurf. is the point closest to the matching point on the 3D model 10a, and N is the number of points)

FIG. 4 shows an RMSE value of 0.171.

Meanwhile, the matching verifier 45b may calculate a distance between the landmark point LP and the current position of the tip of the probe 50 as the matching result, and generate the matching verification information based on the calculated distance. Referring to FIG. 4, the landmark point LP is displayed with gray color in the second image, and a distance value of 28.80 mm between the landmark point LP and the current position of the tip of the probe 50 is displayed in a fourth area. This value is varied as the tip of the probe 50 is changed in position.

Figure 8:
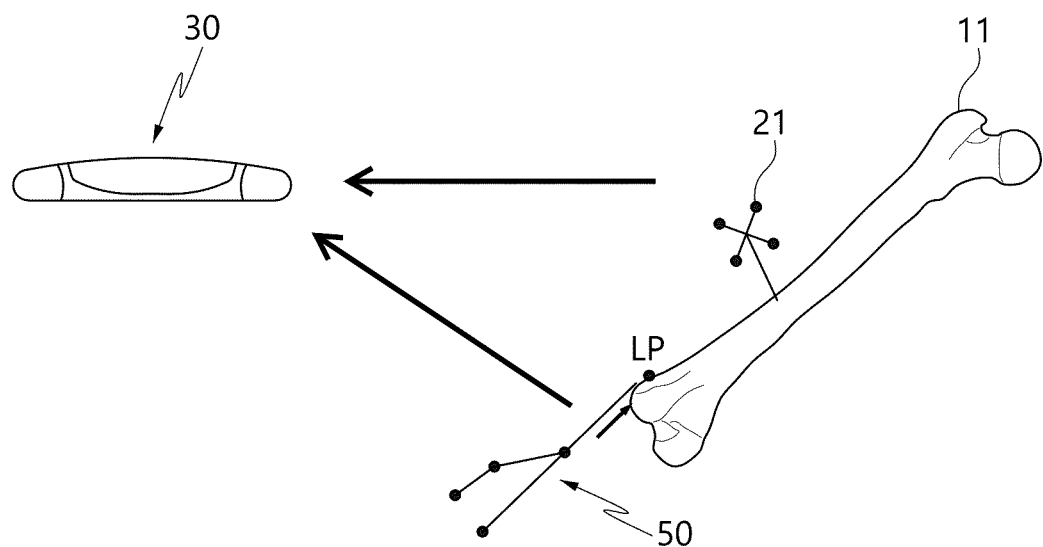
FIG. 8 shows a case where a probe tip is moved to a landmark point according to an embodiment of the disclosure, and corresponding matching verification information is shown in FIG. 9.
Figure 9:
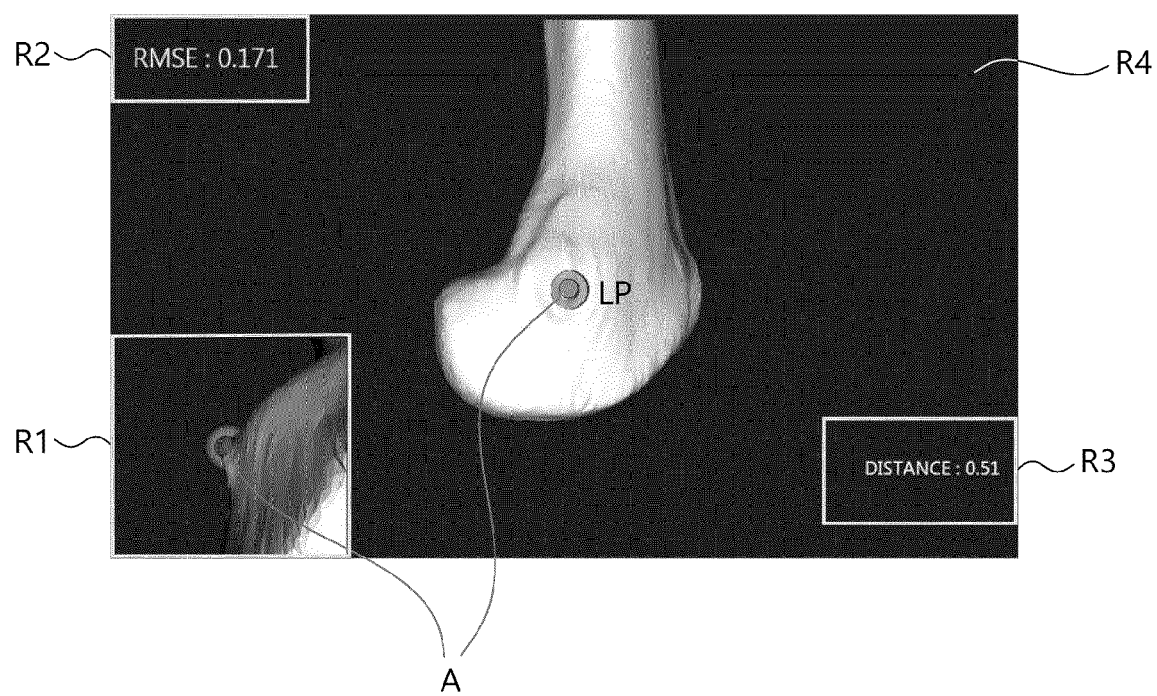

FIG. 8 shows a case where the tip of the probe 50 is moved to the landmark point LP, and FIG. 9 shows the corresponding matching verification information. The 3D graphic icon A is displayed overlapping with the landmark point LP in the first image and the second image, and a calculated distance of 0.51 mm between the landmark point LP and the tip of the probe 50 is displayed in the fourth area. In the first image, the 3D graphic icon A appears in a semicircular shape according to the posture of the probe 50, and thus it is intuitively understood that the matching suitability is high at the corresponding point. Instead of the distance from the landmark point LP, a distance between the point at which the tip of the probe 50 is located corresponding to the movement of the probe 50 and the point closest thereto on the 3D model 10a may alternatively be calculated and displayed. In this case, this value makes it easy to check the matching suitability at the corresponding point.

As above, according to the disclosure, the matching suitability is expressed visually in addition to the quantitative value, so that a user can intuitively know a matching degree.

Figure 10:
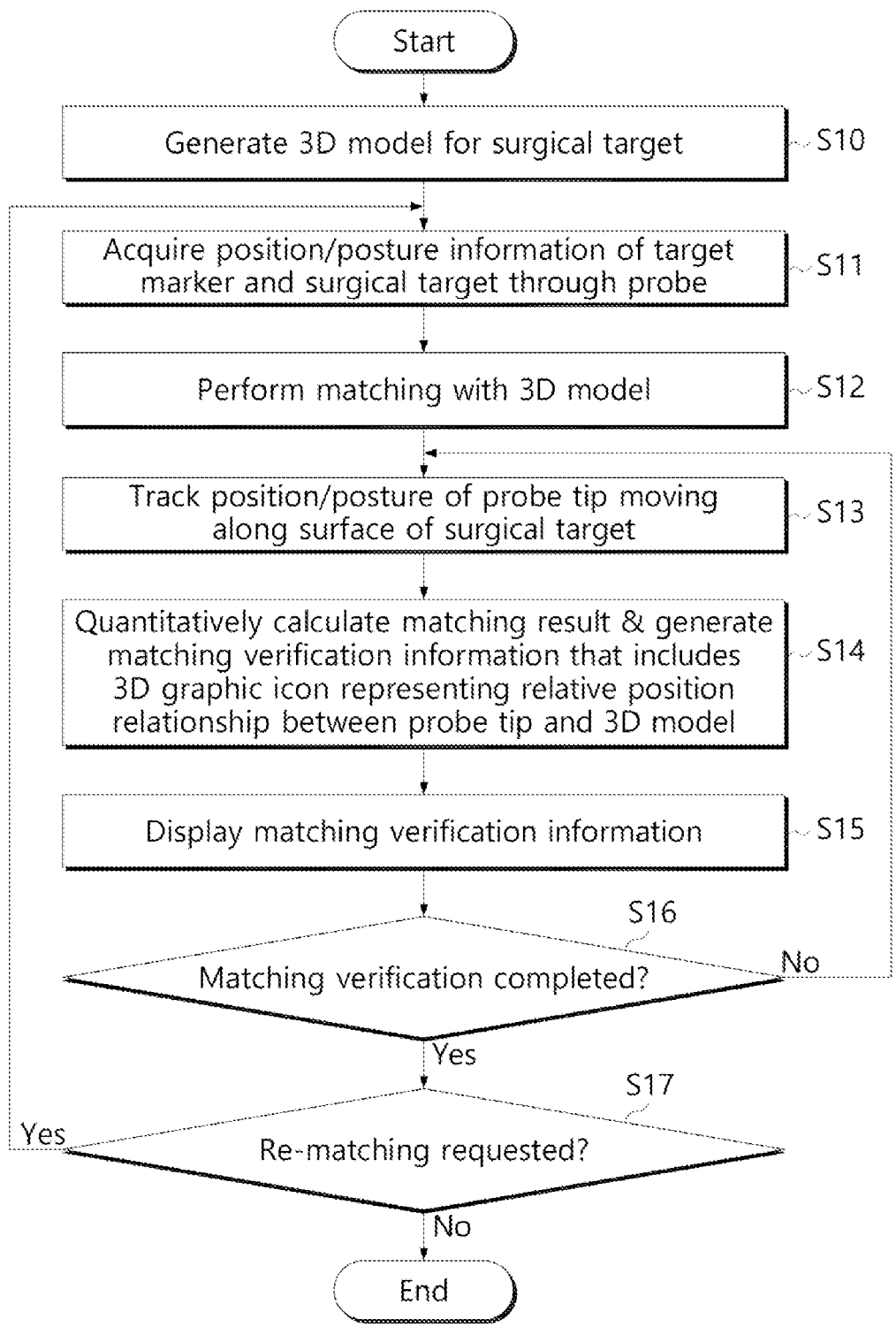
FIG. 10 is a flowchart showing a method of verifying matching of a surgical target through a matching verification apparatus according to an embodiment of the disclosure.

FIG. 10 is a flowchart showing a method of verifying matching of the surgical target 10 or 11 through the matching verification apparatus 40 according to an embodiment of the disclosure. Repetitive descriptions to those of the foregoing embodiments will be avoided as necessary.

Referring to FIG. 10, the 3D model 10a of the surgical target 10 or 11 is first generated based on an image or the like acquired by capturing the surgical target 10 or 11 (S10). The 3D model 10a is stored in the memory 44. The matching verification apparatus 40 receives the position and posture information of the surgical target 10 or 11 and the target marker 21 attached to the surgical target 10 or 11 acquired through the tracker 30 (S11). The position/posture information of the surgical target 10 or 11 may be acquired by various methods. According to an embodiment of the disclosure, the probe 50 is used to acquire the position/posture information of the surgical target 10 or 11.

The target matcher 45a derives a correlation of the position and posture between the surgical target 10 or 11 and the target marker 20 or 21 from the position and posture information of the target marker 21 attached to the surgical target 10 or 11 and the probe 50 received through the tracker 30, thereby performing the matching with the 3D model 10a (S12). In this case, the plurality of preset points are indicated by the probe 50, thereby performing the matching procedure.

When the matching is completed, the matching verifier 45b generates matching verification information about a matching result, and the display unit 43 displays the matching verification information. Meanwhile, the tracker 30 tracks the position/posture of the tip of the probe 50 moving along the surface of the surgical target 10 or 11 and transmits the tracked position/position to the matching verification apparatus 40 (S13). The matching verifier 45b generates the matching verification information that includes the 3D graphic icon A representing a relative positional relationship between the tracked position of the tip of the probe 50 and the 3D model 10a (S14). Further, the matching verifier 45b calculates the matching result as a quantitative value and generates the matching verification information including the quantitative value (S14).

The matching verification information generated through the matching verifier 45b is displayed on the display unit 43 (S15). Thus, a user can intuitively recognize the relative positional relationship between the 3D model 10a and the tip of the probe 50 based on the shape of the 3D graphic icon A represented with a plurality of overlapped spheres having different radii.

Further, not a single point but a series of areas of the surgical target 10 or 11 may be scratched with the probe 50 while changing the position and posture of the probe 50 in order to verify the matching suitability while checking the shape of the 3D graphic icon A.

When the matching verification procedure is completed (S16), it is identified whether re-matching is needed. An image matching apparatus may forcibly perform the matching again with regard to an area, in which the re-matching is required, when the quantitatively calculated value does not satisfy a certain reference value, or a user may make a request for the re-matching when it is identified that the matching degrees of the points checked by the scratching with the probe 50 are low (S17). In this case, the matching may be performed again from the beginning, or only the view corresponding to the area, in which the re-matching is required, may be subjected to the matching again.

Although it has been described above that all elements constituting an embodiment of the disclosure are combined into a single unit or coupled to be operated as a single unit, the disclosure is not necessarily limited to such an embodiment. In other words, at least two elements may be selectively combined and operate without departing from the scope of the disclosure. In addition, each of the elements may be implemented as independent hardware, but some or all of the elements may be selectively combined with each other, so that they can be implemented as a computer program having program modules for executing some or all of the functions combined in one or more pieces of hardware. Codes and code segments forming the computer program can be easily conceived by an ordinarily skilled person in the technical field of the disclosure. Such a computer program may implement the embodiments of the disclosure as being stored in computer readable media, and being read and executed by a computer. The media for the computer program may include magnetic recording media, and optical recording media.

Further, terms, such as "include," "comprise" or "have" mean the presence of a corresponding element unless otherwise specifically described, and should be construed to include one or more other elements without precluding the presence of them. Unless otherwise defined, all the terms including the technical or scientific terms have the same meanings as understood by a person having ordinary knowledge in the art to which the disclosure pertains. General terms that are defined in a dictionary should be construed to have meanings that are consistent in the context of the related art, and will not be interpreted as having an idealistic or excessively formalistic meaning unless otherwise clearly defined in the disclosure.

Although the embodiments of the disclosure have been described for illustrative purposes, it will be appreciated by a person having ordinary knowledge in the art that various modifications and changes can be made without departing from essential characteristics of the disclosure. Accordingly, the embodiments disclosed in the disclosure are merely to not limit but describe the technical spirit of the disclosure, and the technical spirit of the disclosure is not limited by these embodiments. Further, the scope of the disclosure should be construed based on the appended claims, and all of the technical ideas within the scope equivalent to the appended claims should be also construed as being included in the scope of the disclosure.

The invention claimed is:

1. A method of verifying matching of a surgical target, the method comprising:
   preparing a three-dimensional (3D) model comprising shape information about the surgical target by a matching verification apparatus;
   acquiring information about positions and postures of the surgical target and a target marker attached to the surgical target through a tracker by a matching verification apparatus;
   performing matching with the 3D model by deriving a correlation in position and posture between the surgical target and the target marker by a matching verification apparatus;
   tracking change in the position and posture of a probe tip moving along a surface of the surgical target by a matching verification apparatus; and
   generating matching verification information comprising a 3D graphic icon, which represents a relative positional relationship between the probe tip and the 3D model, corresponding to change in at least one of the position and posture of the probe tip, and displaying the matching verification information as an image by a matching verification apparatus;
   wherein the generating the matching verification information and displaying the image comprises generating the 3D graphic icon, which represents a plurality of spheres different in radius from each other and using the position of the probe tip as a center, and displaying the 3D graphic icon on the 3D model.

2. The method of claim 1, wherein the generating the matching verification information and displaying the image comprises changing a shape of the 3D graphic icon to represent the relative positional relationship between the position of the probe tip and the surface of the 3D model by a matching verification apparatus.

3. The method of claim 1, wherein the generating the matching verification information and displaying the image comprises displaying the image varied in viewpoint depending on change in the position or posture of the probe tip by a matching verification apparatus.

4. The method of claim 1, wherein the image showing the matching verification information comprises a first area in which a first image varied in viewpoint for the 3D model depending on change in the position or posture of the probe tip is displayed, and a second area in which a second image is displayed with at least one fixed viewpoint for the 3D model.

5. The method of claim 1, wherein the plurality of spheres are represented to be visually distinguished from each other.

6. The method of claim 1, further comprising quantitatively calculating and displaying a result of the matching by a matching verification apparatus,
wherein the quantitatively calculating and displaying the result of the matching by a matching verification apparatus comprises at least one of:
   calculating and displaying a deviation of a distance between a plurality of points on the surgical target acquired for the matching and a plurality of points on the corresponding 3D model by a matching verification apparatus;
   calculating and displaying a distance between a point at which the probe tip is located corresponding to movement of the probe and a landmark point on the 3D model by a matching verification apparatus; and
   calculating and displaying a distance between a point at which probe tip is located corresponding to movement of the probe and a corresponding point on the 3D model by a matching verification apparatus.

7. An apparatus for verifying matching of a surgical target, the apparatus comprising:
   a signal receiver configured to receive information about positions and postures of the surgical target and a target marker attached to the surgical target, acquired through a tracker;
   a target matcher configured to perform the matching with a three-dimensional (3D) model for the surgical target by deriving a correlation in position and posture between the surgical target and the target marker; and
   a matching verifier configured to generate matching verification information comprising a 3D graphic icon, which represents a relative positional relationship between the probe tip and the 3D model, based on change in the information about the position and posture of the probe tip moving along a surface of the surgical target, received through the signal receiver;
   wherein the matching verifier generates the 3D graphic icon, which represents a plurality of spheres different in radius from each other and using the position of the probe tip as a center, and displays the 3D graphic icon on the 3D model.

8. The apparatus of claim 7, wherein the plurality of spheres are represented to be visually distinguished from each other.

9. The apparatus of claim 7, wherein the matching verifier generates the matching verification information so that a first image having at least one fixed viewpoint for the 3D model and a second image varied in viewpoint depending on change in the position and posture of the probe tip can be respectively displayed in separate areas.

10. A system for verifying matching of a surgical target, the system comprising:
   a tracker configured to track positions and postures of a target marker attached to the surgical target and a probe;
   a memory configured to store a three-dimensional (3D) model having shape information about the surgical target acquired before surgery;
   a target matcher configured to perform matching with the 3D model by deriving a correlation in position and posture between the surgical target and the target marker attached to the surgical target;
   a matching verifier configured to generate matching verification information comprising a 3D graphic icon, which represents a relative positional relationship between the probe tip and the 3D model, based on change in the information about the position and posture of the probe tip moving along a surface of the surgical target, acquired by the tracker; and a display unit configured to display an image based on the matching verification information;

wherein the matching verifier generates the 3D graphic icon, which represents a plurality of spheres different in radius from each other and using the position of the probe tip as a center, and displays the 3D graphic icon on the 3D model.

11. The system of claim 10, wherein the plurality of spheres are represented to be visually distinguished from each other.

* * * * *